United States Patent
Ragsdale (10) Patent No.: US 7,750,605 B2
(45) Date of Patent: Jul. 6, 2010

(54) CONTROLLING AN ELECTRICAL SIGNAL SENT TO A SAMPLE LOAD USING A PULSE MODULATED RESISTANCE

(75) Inventor: Charles W. Ragsdale, Concord, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 21 days.

(21) Appl. No.: 11/857,679

(22) Filed: Sep. 19, 2007

(65) Prior Publication Data
US 2008/0106238 A1    May 8, 2008

Related U.S. Application Data

(60) Provisional application No. 60/826,422, filed on Sep. 21, 2006.

(51) Int. Cl.
    H02J 7/00    (2006.01)
(52) U.S. Cl. .................................................. 320/166
(58) Field of Classification Search ............... 320/166, 320/167; 323/242
    See application file for complete search history.

(56) References Cited

U.S. PATENT DOCUMENTS

| | | | | |
|---|---|---|---|---|
| 3,775,759 | A * | 11/1973 | Armitage et al. ............... 360/45 |
| 4,471,276 | A * | 9/1984 | Cudlitz ........................ 388/811 |
| 4,484,122 | A * | 11/1984 | Day et al. ..................... 318/663 |
| 4,520,296 | A * | 5/1985 | Lepper et al. ............. 318/400.3 |
| 4,540,944 | A * | 9/1985 | Watanabe .................... 327/101 |
| 4,946,793 | A * | 8/1990 | Marshall, III ............ 435/285.2 |
| 5,027,083 | A * | 6/1991 | Kutzavitch et al. .......... 330/284 |
| 5,170,429 | A | 12/1992 | Stocklin et al. |
| 5,269,937 | A | 12/1993 | Dollinger et al. |
| 5,363,070 | A * | 11/1994 | Arimoto ...................... 333/100 |
| 5,642,035 | A | 6/1997 | Ragsdale |
| 5,656,926 | A | 8/1997 | Ragsdale |
| 5,729,426 | A | 3/1998 | Ragsdale |
| 5,891,179 | A | 4/1999 | Er et al. |
| 6,258,592 | B1 * | 7/2001 | Ragsdale et al. ......... 435/285.2 |
| 6,356,086 | B1 | 3/2002 | Cook et al. |
| 6,771,082 | B2 | 8/2004 | Ragsdale et al. |
| 6,798,175 | B2 * | 9/2004 | Hanada et al. ............... 320/166 |

(Continued)

FOREIGN PATENT DOCUMENTS

WO    WO 04/050866 A1    6/2004

OTHER PUBLICATIONS

U.S. Appl. No. 11/567,373, filed Dec. 6, 2006.

(Continued)

*Primary Examiner*—Edward Tso
*Assistant Examiner*—Arun Williams
(74) *Attorney, Agent, or Firm*—Townsend, Townsend and Crew LLP; David B. Raczkowski (57) ABSTRACT

Systems, methods, apparatus, and circuits for controlling an electrical signal transmitted to a sample load are provided. The electrical signal produced by a capacitor is controlled via a control signal sent to a variable resistance device that is connected in parallel with the sample load. The variable resistance device includes a resistance and a switch in series. The control signal opens and closes the switch, thus providing a variable resistance based on the amount of time the switch is closed.

28 Claims, 5 Drawing Sheets

U.S. PATENT DOCUMENTS

| | | |
|---|---|---|
| 6,856,119 B2 * | 2/2005 | Crawford .................... 320/166 |
| 7,054,685 B2 | 5/2006 | Dimmer et al. |
| 2003/0026092 A1 * | 2/2003 | Reese et al. ................. 362/183 |
| 2003/0214269 A1 * | 11/2003 | Shiue et al. ................. 320/166 |
| 2004/0171962 A1 | 9/2004 | Leveque et al. |
| 2006/0115888 A1 | 6/2006 | Gamelin et al. |
| 2007/0194759 A1 * | 8/2007 | Shimizu et al. ............. 320/166 |
| 2008/0024079 A1 * | 1/2008 | Matsubara et al. .......... 318/376 |

OTHER PUBLICATIONS

U.S. Appl. No. 60/826,422, filed Sep. 21, 2006.

U.S. Appl. No. 11/567,438, filed Dec. 6, 2006.

* cited by examiner

CONTROLLING AN ELECTRICAL SIGNAL SENT TO A SAMPLE LOAD USING A PULSE MODULATED RESISTANCE

CROSS-REFERENCES TO RELATED APPLICATIONS

This application claims the benefit of U.S. Provisional Patent Application 60/826,422 entitled "RESISTOR PULSE MODULATION," by Charles W. Ragsdale, filed Sep. 21, 2006, the entire contents of which are incorporated herein by reference.

BACKGROUND

The present invention relates generally to controlling electrical signals and more particularly to systems and methods for controlling the shape of an electrical pulse in electroporation systems.

It is known that exposure of cells or other biological molecules to intense electric fields for brief periods of time temporarily destabilizes membranes. This effect has been described as a dielectric breakdown due to an induced transmembrane potential, and has been termed "electroporation". Among the procedures that use electroporation are the production of monoclonal antibodies, cell-cell fusion, cell-tissue fusion, insertion of membrane proteins, and genetic transformation.

The cells or tissue are exposed to electric fields by administering one or more direct current pulses. These pulses are administered in an electrical treatment that results in a temporary membrane destabilization with minimal cytotoxicity. The intensity of the electrical treatment is typically expressed in terms of the field strength of the applied electric field. This electric field strength is defined as the voltage applied to the electrodes divided by the distance between the electrodes. Electric field strengths used in electroporation typically range from 1000 to 5000 V/cm.

For efficient electroporation, it is necessary to control the shape, e.g. time constant of the electrical pulse. For example, electroporation itself occurs within a narrow range of parameters, such as pulse voltage and pulse duration, which is exhibited by a narrow window between electrocution and little or no electroporation. If a pulse with too long a duration or too high a field strength is used, the cells may be lysed (destroyed). If the duration or field strength of a pulse is too low, electroporation efficiency is lost. As an added difficulty, the optimal voltage and time constant varies with the type of cell. The current emphasis on using electroporation to study cells that are sensitive and difficult to transvect makes the control of electroporation conditions particularly important.

One problem in selecting the electroporation parameters is that the sample itself (cells plus buffer) is a significant factor in the load imposed on an electroporator and can have a wide range of resistance values. To provide the desired shape, a selection of capacitors (used to store charge for delivery to the sample) may be used to determine a time constant. Parallel resistors can also be switched-in to supplement the adjustment precision. Switchable high-voltage power resistors are large and costly, however. Additionally, the precision of adjustment achievable is still rather coarse to be able to reduce the number of such resistors and switching elements.

It is, therefore, desirable to provide systems and methods for controlling the shape of the electrical signal in a more efficient and continuous manner.

BRIEF SUMMARY

Accordingly, the present invention provides systems, methods and circuits for controlling an electrical signal transmitted to a sample load. The electrical signal produced by a capacitor is controlled via a control signal sent to a variable resistance device that is connected in parallel with the sample load. In one aspect, the variable resistance device includes a resistance and a switch in series. The control signal opens and closes the switch, thus providing a variable resistance based on the amount of time the switch is closed.

The variable resistance device may have a constant resistance during an electrical signal, i.e. the amount of time the switch is closed over a certain time period remains constant, or the resistance may vary over a time period for the electrical signal. For example, in an embodiment where the control signal is a pulse width modulated signal, the duty cycle may stay constant or change during the electrical signal.

The resistance of the variable resistance device may be a combination of resistors. Also, additional resistances and switches may be in parallel with the sample load as well as the other resistance and switch combinations. All of the resistance and switch combinations may use the same control signal or use different control signals. In one embodiment, the switches are transistors, such as an insulated gate bipolar transistor.

As user herein, an electrical signal may be a periodic waveform or be non-periodic, such as a pulse, and each may have different shapes to the waveform, such a square, sine or triangular wave, or an exponential decaying pulse. In one embodiment, an exponentially decaying electrical pulse with a time constant $\tau$ tunable with the control signal is provided to a sample load.

Reference to the remaining portions of the specification, including the drawings claims and Appendices, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

DETAILED DESCRIPTION OF EXEMPLARY EMBODIMENTS

The present invention provides systems, methods and circuits for controlling an electrical signal transmitted to a sample load. Embodiments utilize a capacitor to produce an electrical signal, which is controlled by a variable resistor device connected with the sample load. Although embodiments are directed to producing an electrical signal in an electroporation, one skilled in the art will appreciate that embodiments may be used in any system with an innate capacitor, such as power supplies and function generators.

Figure 1:
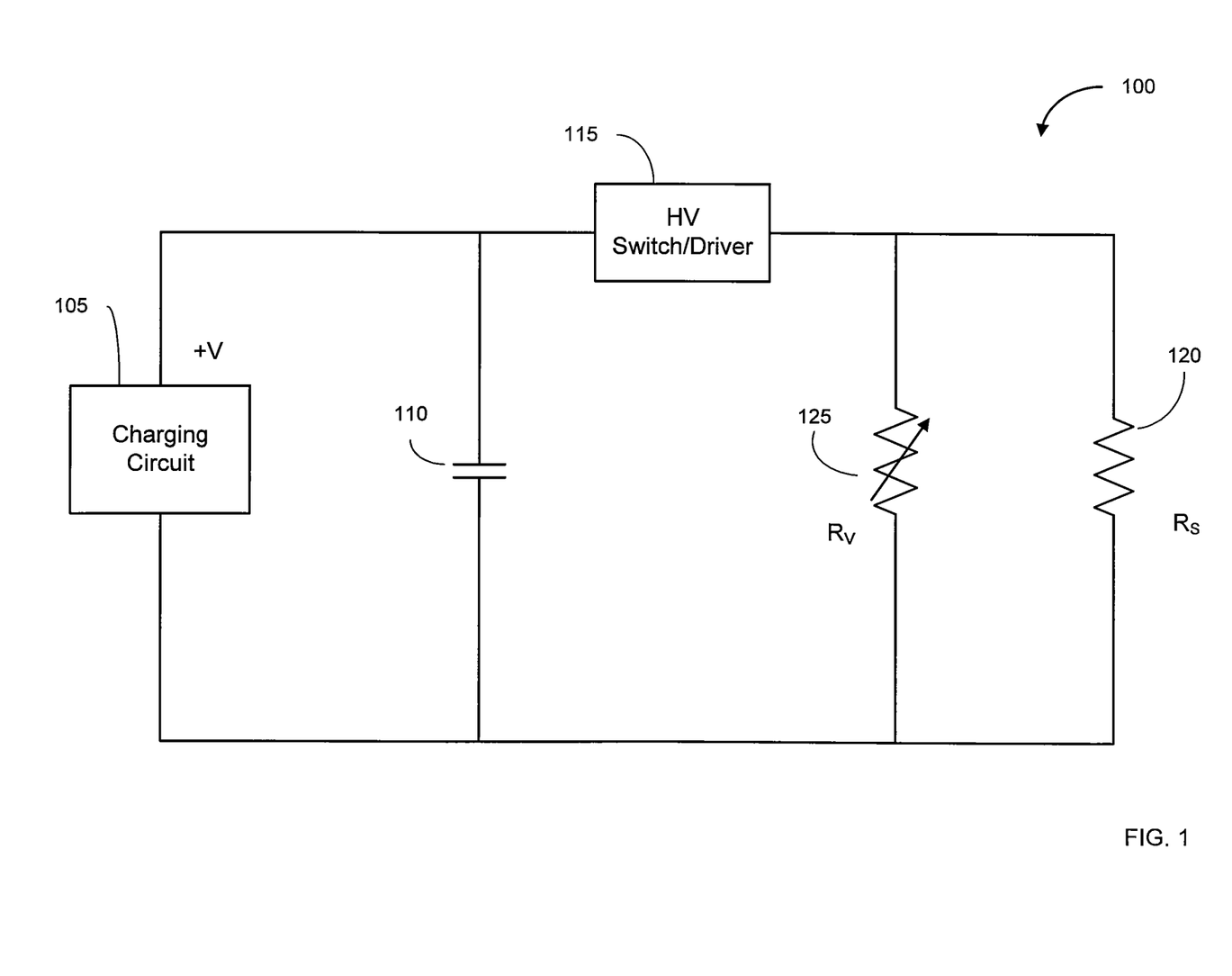
FIG. 1 illustrates a system having a variable resistance device according to an embodiment of the present invention.

FIG. 1 illustrates a system 100 according to an embodiment of the present invention. System 100 produces an electrical signal for sample load 120. A charging circuit 105 is connected with a capacitor 110 so as to charge capacitor 110 when switch 115, e.g. a high voltage (HV) switch, is open. In one aspect, charging circuit 105 is a power supply or some other constant power source. HV switch 115 connects capacitor 110 to sample load $R_S$ 120 and a variable resistor $R_V$ 125, which is connected in parallel with $R_S$ 120.

Once charging circuit 105 charges the capacitor 110 to a desired voltage HV switch 115 is closed. HV switch 115 may also be a driver with programmable parameters, such as number of pulses, pulse duration, and bursts of pulses. At this point, an electrical signal is transmitted to $R_S$ 120 and to $R_V$ 125. In one aspect the electrical signal is an exponentially decaying pulse, a truncated exponentially decaying pulse, or a square wave signal with droop.

The value of the resistance of $R_V$ 125 may be tuned to control the electrical signal. For example, for an exponentially decaying pulse, the resistance of $R_V$ 125 may be automatically determined such that a desired time constant $\tau=CR$ is substantially equal to the desired pulse duration, wherein $R=(R_S \times R_V)/(R_S+R_V)$ and C is the capacitance of capacitor 110.

In one embodiment, system 100 is an electroporator system. In this embodiment, the time constant may be chosen specifically based on the cells or other type of biomolecules in the sample load. As some cells may be sensitive or hard to transvect, a precisely controlled time constant can promote successful electroporation.

Figure 2:
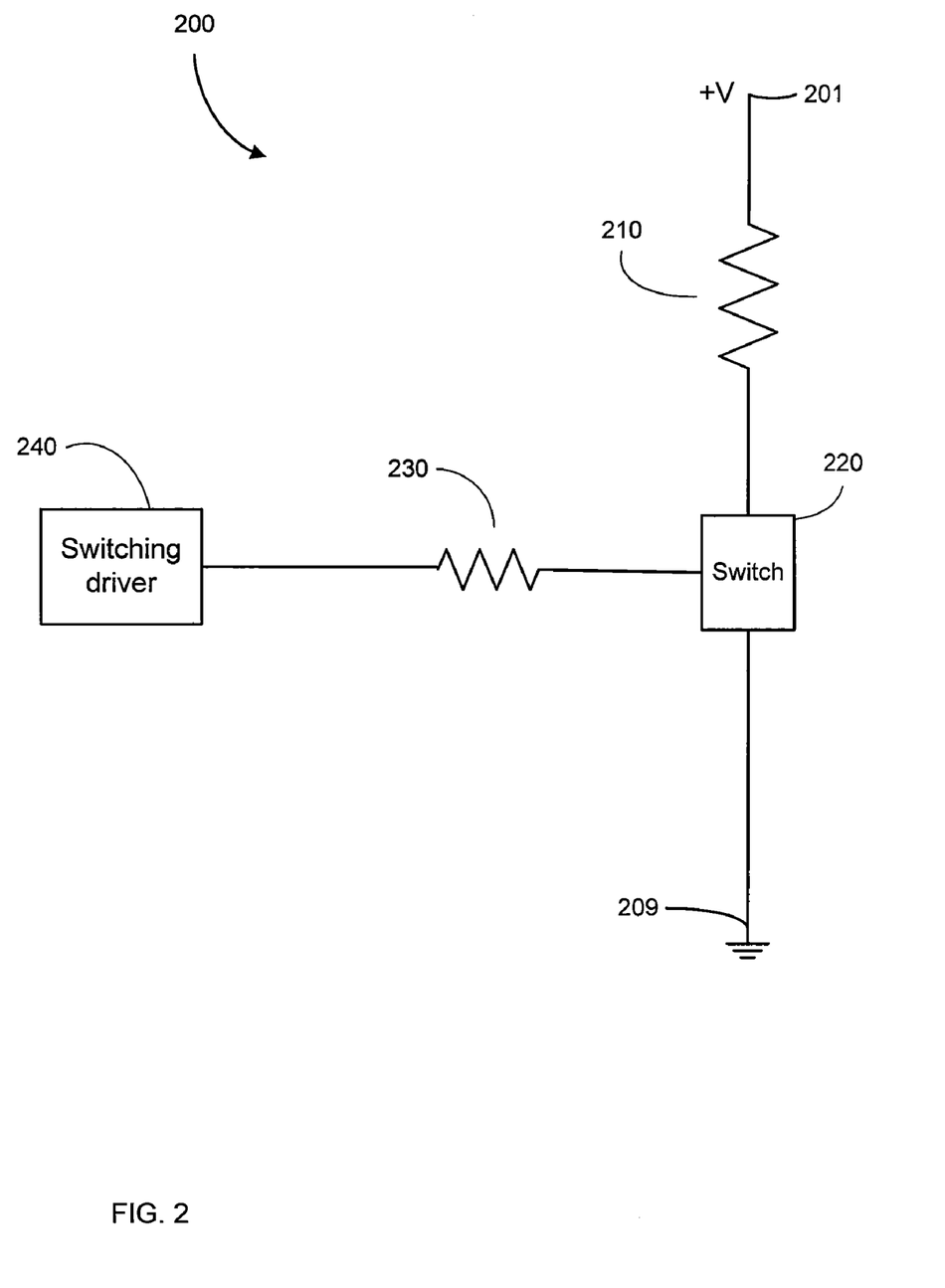
FIG. 2 illustrates a variable resistance device according to an embodiment of the present invention.

FIG. 2 illustrates a variable resistance device 200 according to an embodiment of the present invention. Resistance 210 has one terminal connected with a switch 220, which is controlled by a switching driver 240. In one aspect, a resistance 230 may be connected between switching driver 240 and switch 220 to provide greater stability. Resistance 220 may be composed of one resistor or multiple resistors in any combination as known to one skilled in the art.

One end 201 of device 200 is at a higher potential than another end 209. Thus, current flows from top to bottom when switch 220 is closed. However, when switch 220 is open, no current flows. Switching driver 240 transmits one or more control signals to switch 220 to control whether switch 220 is open or closed. By controlling when current flows through resistance 210, the effective resistance of resistance 210 can be controlled.

For example, if resistor 210 is 50 ohms, which is generally ideal for a high-throughput electroporator, a 100% duty cycle would result in 50 ohms of resistance. A 100% duty cycle corresponds to switch 220 always being closed and resistor 210 being switched-in continuously. However, a 10% duty cycle that switches-in resistor 210 ten percent of the time would result in a resistance of 10×50=500 ohms. The general formula for the effective resistance is 100/(duty cycle percentage)×actual resistance. Since the switching device controlling the connection of the resistor is either on or off, its losses are low, and it never needs to act as an analog control element.

In one embodiment, the control signals from switching driver 240 are pulse width modulated. In one aspect, switch 220 is a transistor, such as an IGBT, MOSFET, or other suitable transistor. Resistance 230 may be connected to the gate of the transistor. In another aspect, switch 220 is a silicon controlled rectifier.

Figure 3:
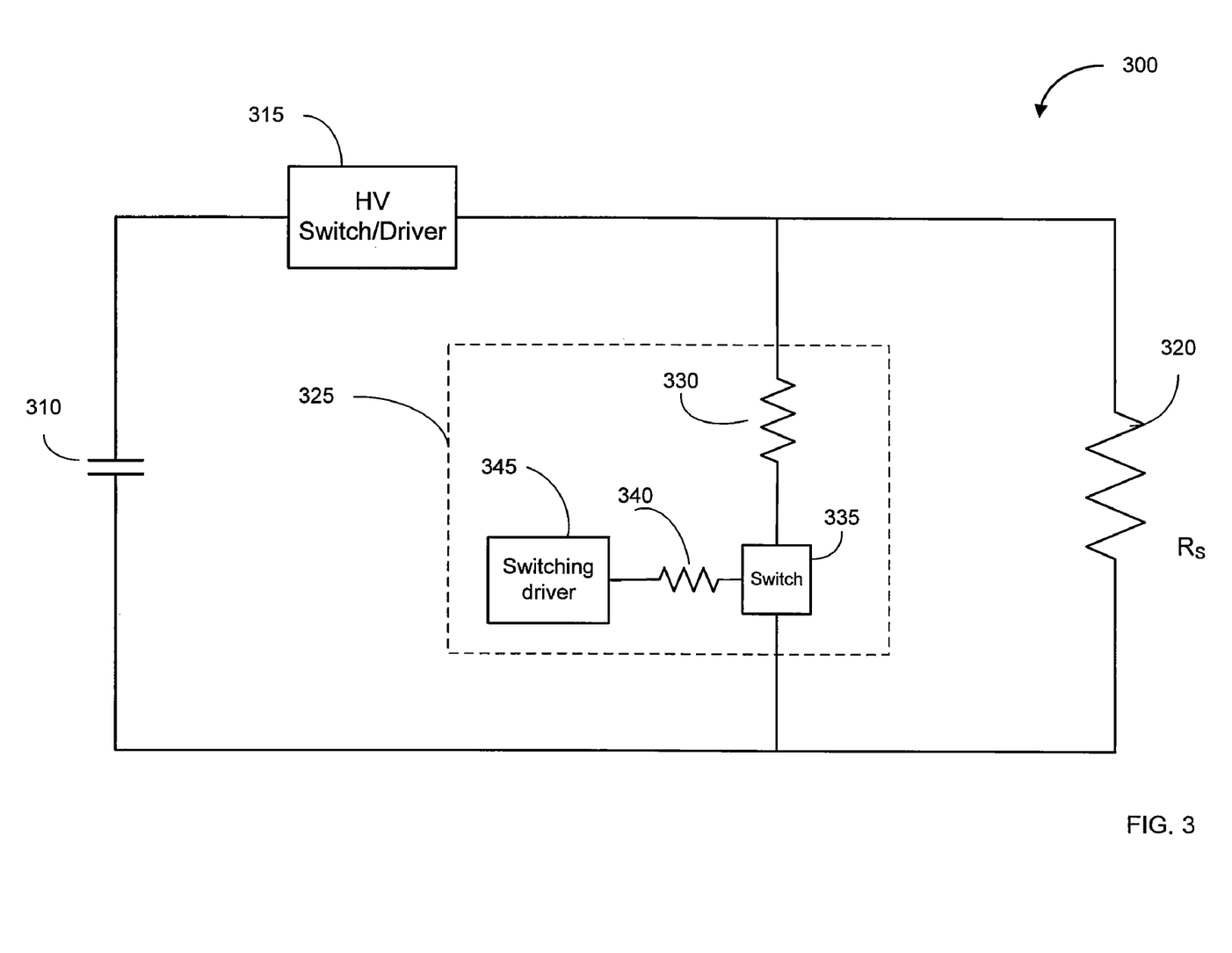
FIG. 3 illustrates a circuit that provides a controllable electrical signal according to an embodiment of the present invention.

FIG. 3 illustrates a circuit 300 according to an embodiment of the present invention. Circuit 300 uses a variable resistance device 325 to control an electrical signal from capacitance 300. In one aspect, device 200 may be used for device 325. Capacitance 310 may be composed of multiple capacitors in any suitable arrangement, such in series and/or in parallel with each other.

In one embodiment, where the electrical signal is an exponentially decaying pulse, the duty cycle of switch 335 may be adjusted to achieve a desired time constant. For example, if a 7 msec time constant is desired then the required resistance for device 325 may be calculated. If C=50 µF, then the combined resistance R=7 msec/50 µF=140Ω. If $R_S$ was 200Ω, then $R_V$ would be 467Ω. To achieve 467Ω from a resistance of 50Ω for resistance 330, then the duty cycle=100×50/467, which give a duty cycle of 10.7%.

In another embodiment, the duty cycle of the control signal from switching driver 545 varies over time. For example, the duty cycle could be smaller at the beginning of an electrical signal so that the voltage of an electrical pulse droops or decreases at a relatively slow rate. After a certain amount of time, the duty cycle could increase so as to increase the current through resistor 330, thus increasing the rate of voltage drop for the electrical pulse. Many different combinations of changing the duty cycle could be made as to achieve many different shapes of waveforms, signals, and pulses.

Figure 4:
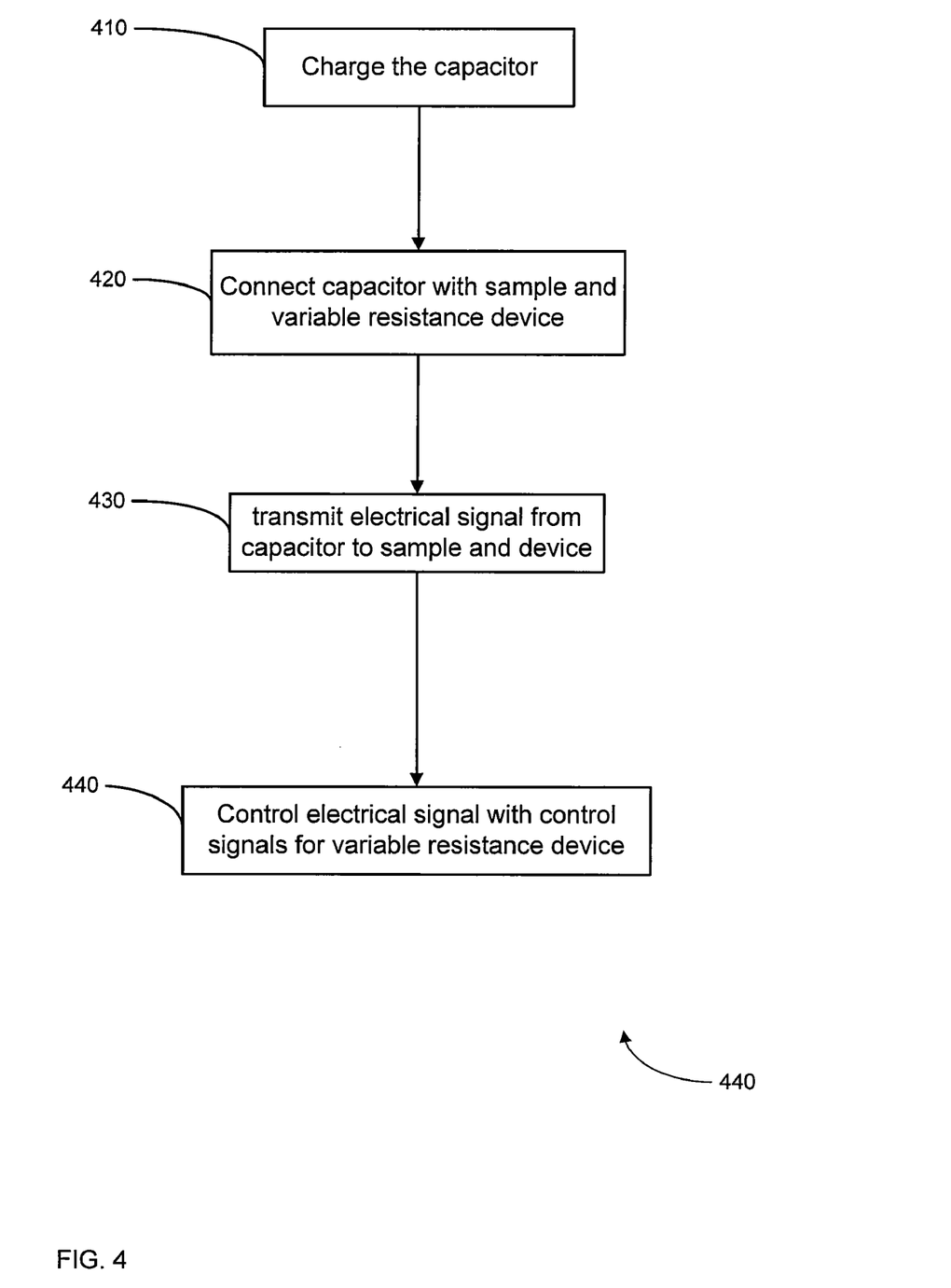
FIG. 4 illustrates a method for controlling an electrical signal transmitted to a sample load according to an embodiment of the present invention.

FIG. 4 illustrates a method of controlling an electrical signal transmitted to a sample load according to an embodiment of the present invention. In step 410, the capacitor is charged by a charging circuit, such as a power supply. In step 420, the capacitor is connected with a sample load and a variable resistance device, such device 325. The connection may be made by an HV switch.

In step 430, an electrical signal is transmitted from the capacitor to the sample and to the variable resistance device. In one aspect, the electrical signal is of any waveform shape, which may at least be partially determined by the HV switch. In step 440, the electrical signal is controlled with the control signals that determine the resistance of the variable resistance device. In one aspect, the higher the control signals make the resistance of the variable resistance device, the slower the voltage of the electrical signal drops.

Figure 5:
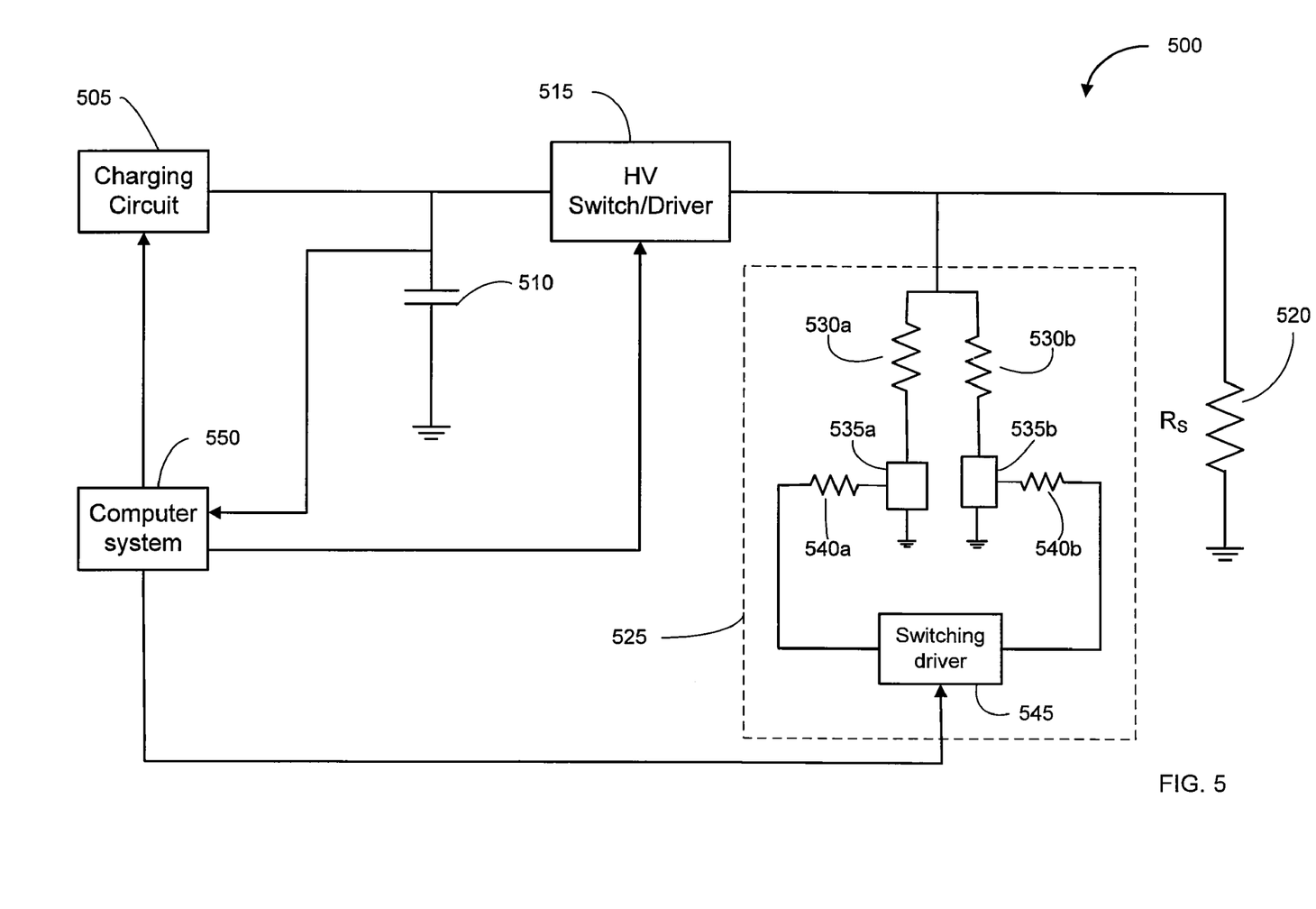
FIG. 5 illustrates a system having a variable resistance device according to an embodiment of the present invention.

FIG. 5 illustrates a system 500 according to an embodiment of the present invention. Charging circuit 505 receives instructions from computer system 550, which may monitor the voltage at capacitor 510. The instructions may include whether to continue to charge capacitor 510 or at what level to charge it. In one embodiment, when the voltage at capacitor 510 reaches a sufficient value, computer system 550 signals a HV driver 515 to connect capacitor 510 to the load sample $R_S$ 520 and variable resistor device 525. Computer system 550 may include one or more processors, memory such as RAM, a user interface, and docking ports for receiving external memory units, such as a CD or DVD.

Variable resistance device 525 has two switches 535a and 535b, e.g. two IGBT transistors. Each switch 535 drives a pair of tandem connected power resistors 530a and 530b, which may be at the output of an electroporator. In one embodiment, the resistors 530a and 530b are 100Ω, and resistors 540a and 540b are 10Ω. In one aspect, switches 535 are driven by switching driver 545 at a 10 KHz rate with a duty cycle dependent on the desired effective resistance for variable resistance device 525. Accordingly, effective resistances of 50-1500Ω may be achieved. In one aspect, this range is achieved with only about four square inches of board space and perhaps less than $15 worth of parts.

Computer system 550 can program switching driver 545 to drive switches 535 at the proper rate and with the proper duty cycle. In one aspect, switching driver 545 contains a processor which can calculate the proper duty cycle or succession of duty cycles required. In another aspect, computer system 550 could include a driver for driving switches 535.

In one embodiment, a desired time constant of an exponentially decaying electrical pulse can be achieved with an almost continuous adjustability, thus allowing a choice of a time constant with very high precision. In one aspect, capacitor 510 includes electronically selectable capacitors, which facilitates the almost continuous range of time constants. For a square wave, the droop level in the positive voltage can also be controlled in a similar manner.

In one aspect, since an electronically pulsed load is only on during the brief pulse, any interference is minimized. Also, in another aspect, since the capacitors can be large and the frequency high, the ripple on the output waveform is low.

While the invention has been described by way of example and in terms of the specific embodiments, it is to be understood that the invention is not limited to the disclosed embodiments. To the contrary, it is intended to cover various modifications and similar arrangements as would be apparent to those skilled in the art. Therefore, the scope of the appended claims should be accorded the broadest interpretation so as to encompass all such modifications and similar arrangements.

What is claimed is:

1. A method of controlling an electrical pulse transmitted to a sample load containing biological molecules, the method comprising:
   charging a capacitance;
   subsequent to the charging, connecting the capacitance with the sample load and a variable resistance device connected in parallel with the sample load containing biological molecules, the variable resistance device including:
   a first resistor;
   a first switch connected in series with the first resistor, wherein the first switch is opened and closed by a first control signal;
   transmitting an electrical pulse from the capacitance to the sample load and the variable resistance device; and
   controlling the electrical pulse by opening and closing, with the first control signal, the first switch a plurality of times during transmission of the electrical pulse.

2. The method of claim 1, wherein the first control signal opens and closes the first switch such that the variable resistance device has a constant resistance while the electrical pulse is transmitted.

3. The method of claim 2, wherein the constant resistance is specified by a user.

4. The method of claim 1, wherein the first control signal is a pulse width modulated signal, wherein a resistance of the variable resistance device is controlled by the pulse width modulated signal.

5. The method of claim 1, wherein the first control signal opens and closes the first switch such that the resistance of the variable resistance device varies while the electrical pulse is transmitted.

6. The method of claim 5, wherein the first control signal is a pulse width modulated signal, and wherein the pulse widths change as to vary the resistance of the variable resistance device while the electrical pulse is transmitted.

7. The method of claim 1, wherein the electrical pulse is an exponentially decaying pulse, further comprising adjusting the first control signal to achieve a desired time constant τ for the exponential decay.

8. The method of claim 1, wherein the electrical pulse is a pulse of a square wave.

9. The method of claim 1, wherein the variable resistance device further includes one or more other resistors in series with the first resistor.

10. The method of claim 1, wherein the variable resistance device further includes:
    a second resistor connected in parallel with the first resistor; and
    a second switch connected in series with the second resistor, wherein the second switch is opened and closed by a second control signal.

11. The method of claim 10, wherein the variable resistance device further includes:
    one or more additional resistors, each connected in parallel with the first and second resistors and with the other additional resistors; and
    one or more additional switches, each connected in series with one of the additional resistors.

12. The method of claim 1, wherein the sample load contains biological molecules that are electroporated by the electrical pulse.

13. A circuit configured to provide a controllable electrical pulse to a sample load containing biological molecules, the circuit comprising:
    a capacitance selectively connected with the sample load; and
    a variable resistance device connected in parallel with the sample load containing biological molecules, the variable resistance device including:
    a first resistor; and
    a first switch in series with the first resistor, wherein the first switch is opened and closed by a first control signal;
    wherein when the capacitance is charged and selected to be connected with the sample load, an electrical pulse is transmitted from the capacitance to the sample load and the variable resistance device, and wherein the first control signal controls the electrical pulse by opening and closing the first switch a plurality of times during transmission of the electrical pulse.

14. The circuit of claim 13, wherein the capacitance is connected in parallel with sample load.

15. The circuit of claim 13, wherein the first control signal is a pulse width modulated signal, wherein a resistance of the variable resistance device is controlled by the pulse width modulated signal.

16. The circuit of claim 13, wherein the first control signal opens and closes the first switch such that the resistance of the variable resistance device varies while the electrical pulse is transmitted.

17. The circuit of claim 13, wherein the first control signal is a pulse width modulated signal, and wherein the pulse widths change as to vary the resistance of the variable resistance device while the electrical pulse is transmitted.

18. The circuit of claim 13, wherein the electrical pulse is an exponentially decaying pulse and the first control signal is determined by a computer system to achieve a desired time constant τ for the exponential decay.

19. The circuit of claim 13, wherein the variable resistance device further includes one or more other resistors in series with the first resistor.

20. The circuit of claim 13, wherein the variable resistance device further includes:
   a second resistor connected in parallel with the first resistor; and
   a second switch connected in series with the second resistor, wherein the second switch is opened and closed by the first control signal.

21. The circuit of claim 20, wherein the variable resistance device further includes:
   one or more additional resistors, each connected in parallel with the first and second resistors and with the other additional resistors; and
   one or more additional switches, each connected in series with one of the additional resistors.

22. An electroporator system for providing a controllable electrical pulse to a sample load containing biological molecules, comprising:
   a capacitance selectively connected with the sample load; and
   a variable resistance device connected in parallel with the sample load, the variable resistance device including:
      a first resistor; and
      a first switch in series with the first resistor, wherein the first switch is opened and closed by a first control signal;
   wherein when the capacitance is charged and selected to be connected with the sample load, an electrical pulse is transmitted from the capacitance to the sample load and the variable resistance device, and wherein the electrical pulse is controlled with the first control signal by opening and closing the first switch a plurality of times during transmission of the electrical pulse, and wherein the electrical pulse causes electroporation of the biological molecules in the sample load.

23. The electroporator system of claim 22, further comprising a charging circuit that charges the capacitance to a specified voltage.

24. The electroporator system of claim 22, further comprising a switching driver that provides the first control signal that determines the resistance of the variable resistance device by opening and closing the first switch.

25. The electroporator system of claim 24, further comprising a high voltage driver for selectively connecting the capacitance to the sample load.

26. The electroporator system of claim 22, wherein the capacitance is not connected to the sample load prior to the capacitance being charged to a desired voltage and is connected to the sample load when the capacitance is charged to a desired voltage.

27. The method of claim 1, further comprising:
   transmitting one or more additional electrical pulses from the capacitance to the sample load and the variable resistance device; and
   controlling the additional electrical pulses by opening and closing, with the first control signal, the first switch a plurality of times during transmission of each respective electrical pulse.

28. The method of claim 7, wherein adjusting the first control signal to achieve a desired time constant $\tau$ includes varying a duty cycle of the first control signal such that the desired time constant $\tau$ is achieved.

* * * * *